(12) United States Patent
Virtanen

(10) Patent No.: US 7,260,428 B2
(45) Date of Patent: Aug. 21, 2007

(54) SHIELD ARRANGEMENT FOR ECG LEAD WIRES

(75) Inventor: Juha Virtanen, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 75 days.

(21) Appl. No.: 10/753,866

(22) Filed: Jan. 8, 2004

(65) Prior Publication Data

US 2004/0210150 A1 Oct. 21, 2004

(30) Foreign Application Priority Data

Jan. 9, 2003 (EP) ................................ 03396003

(51) Int. Cl.
*A61B 5/0428* (2006.01)

(52) U.S. Cl. ...................... 600/509; 600/522; 600/523; 128/901; 128/908

(58) Field of Classification Search ................ 600/508, 600/509, 512, 523, 522; 128/908, 901, 902
See application file for complete search history.

(56) References Cited

U.S. PATENT DOCUMENTS 2,976,462 A * 3/1961 Muller ........................ 361/112
3,521,087 A * 7/1970 Lombardi ..................... 327/322
3,605,728 A * 9/1971 Ogle ............................ 600/508
3,620,208 A * 11/1971 Higley et al. ................. 600/395
4,417,590 A    11/1983 Smith et al.
4,577,639 A * 3/1986 Simon et al. ................. 600/522
4,742,831 A * 5/1988 Silvian ........................ 600/523
4,848,335 A * 7/1989 Manes .......................... 606/35
4,890,630 A * 1/1990 Kroll et al. .................. 600/508
5,042,498 A * 8/1991 Dukes .......................... 600/509
6,553,250 B2   4/2003 Rantala

FOREIGN PATENT DOCUMENTS

WO    WO-01/06923    2/2001

* cited by examiner

*Primary Examiner*—George R. Evanisko
*Assistant Examiner*—Michael Kahelin
(74) *Attorney, Agent, or Firm*—Andrus, Sceales, Starke & Sawall, LLP

(57) ABSTRACT

A grounding arrangement in a system using the same connector for 5- and 12-lead connection in ECG-measurement. If 5-lead configuration is used, the connector elements of the 12-lead connection are used for grounding of lead wire shields through a current limiting circuit exhibiting non-linear voltage-current characteristics.

9 Claims, 4 Drawing Sheets

SHIELD ARRANGEMENT FOR ECG LEAD WIRES

CROSS REFERENCE TO RELATED APPLICATION

The present application claims priority from European Patent Application No. 03396003.0, filed Jan. 9, 2003.

FIELD OF THE INVENTION

The present invention relates to a system for ECG monitoring. In particular, the present invention relates to a novel system and method for grounding of the shields of electrode lead wires.

BACKGROUND TO THE INVENTION

In prior art is known a system for ECG monitoring as represented by the diagram in FIG. 1. In FIG. 1, the same patient P is diagrammatically represented by two pictures of the torso, where the lower picture shows a standard four-point placement of measuring electrodes R, F, L and N (so-called limb electrodes). For the sake of clarity, the upper picture separately shows a standard placement of ECG measuring electrodes, i.e. precordial electrodes $V_1$, $V_2$, $V_3$, $V_4$, $V_5$, $V_6$ on the patient's thorax. Together the limb electrodes and precordial electrodes form a so-called 12-lead connection system. A so-called 5-lead connection system, also used in ECG measurement, consists of limb electrodes together with one of the pre-cordial electrodes, e.g. R, F, L, N and $V_1$.

Each measuring electrode is provided with a signal lead wire 1-10 which are further provided with first connector elements 11. The ECG monitoring system further comprises a collecting connector 13 provided with second connector elements 14 for receiving the first connector elements 11 of the signal lead wire. The collecting connector may reside either in the collecting cable 12 with an adapter 24 at its end or directly at the amplifier unit 16. The system further comprises an ECG apparatus 30.

The circuitry for measuring 5 or 12-lead ECG is presented in FIG. 2. The collecting connector 13 comprises twenty connector elements 14 in all. Placed in the upper row on the left are circular connector elements $14_1$ for the upper part of connector elements 11 providing connections for the signal lead wires 1-5 coming from the limb electrodes R, F, L, N, and one precordial electrode $V_1$. Connected to the circular connector elements 14 in the right-hand part of the upper row are the upper part of connector elements 11 providing connections for the signal lead wires 6-10 coming from the precordial electrodes $V_2$, $V_3$, $V_4$, $V_5$ and $V_6$. The rectangular connector elements $14_2$ in the lower row are for the lower parts of connector elements 11 providing connections for the lead wire shields SH. Connector elements $14_2$ provide a shielding ground connection 39, which in this case is the amplifier ground G. The dual connector elements 11 are consistent with the AAMI standard.

The function of the N-electrode is to equalize the potentials of the patient and the amplifier. For this purpose, the N-electrode is traditionally connected to the amplifier ground G either directly or through a single resistor or a network of resistors and capacitors. The potential difference may be further reduced with an electronic circuit 34 actively driving the potential of the patient closer to the potential of the amplifier, often referred to as right-leg-drive circuit (RLD). This kind of driver includes a current limiting circuit typically adjusted to a maximum current allowed in a single-fault condition (EN60601-1).

Resistors R protect the preamplifiers 35, RLD-circuit 34, and impedance measurement circuit 33 from over-voltages and limit the currents through electrodes in case of defibrillation.

Also in prior art, patent application WO 01/06923 discloses a lead set and connector arrangement system as shown in FIG. 3, which can operate both as a 5-lead measuring system and as a 12-lead measuring system, and in which it is possible to combine the limb-electrode and precordial electrode parts of the collecting connector 13, allowing the same amplifier unit to function alternatively in a 5-lead measuring system with shielded lead wires 37 or in a 12-lead measuring system with unshielded lead wires 38. In this system a small and lightweight collecting connector can be used.

The circuitry for measuring 5 or 12-lead ECG is presented in FIG. 4. In this arrangement, when measuring 12-lead ECG, the circular second connector elements $14_1$ are used for the first connector elements 11 of the lead wires 1-5 coming from the limb electrodes R, F, L, N, and one precordial electrode $V_1$ (un-shielded 12-lead set 38). Connected to the rectangular second connector elements $14_2$ of the lower row are the first connector elements 11 of the lead wires 6-10 coming from the precordial electrodes $V_2$, $V_3$, $V_4$, $V_5$ and $V_6$ (unshielded 12-lead set 38).

In case of 5-lead ECG one possible lead-set configuration consists of AAMI-compatible connectors with shields connected to the lower, rectangular connectors $14_2$ (shielded 5-lead set 37). In this case, analog switches 18-22 inside the amplifier unit may be used to provide shielding ground connection 39 for the lower connector pins $14_2$ and hence for the lead wire shields SH.

Use of shielded signal lead wires has an importance especially in ECG monitoring performed during anesthesia, because surgical operations are often performed using a so-called diathermy device, i.e. an electric surgical knife, whose high-frequency electric current would otherwise confuse the ECG monitoring process, but also in intensive care monitoring, where line voltage interference and electrostatic voltages coupling directly to the lead wires may be a significant problem.

Considering the prior art, there remain unresolved technical problems related to the use of the analog switches 18-22 for providing shielding ground connection for the lead wire shields. When changing over from 5 to 12-lead measuring mode by adding precordial electrodes, a low-impedance current path is created between the right-leg-drive circuit 34 and amplifier ground G, if the precordial electrodes get connected to the amplifier ground G by via analog switches 18-22. Because of small offset voltages always present in this kind of electronics circuit, the output of the RLD circuit may be driven to the current limit, which makes the RLD circuit effectively inoperative. Furthermore, because connection of electrodes and lead wires in this manner is a normal operating procedure, the current limit of the RLD circuit has to be set to conform with the 10 µA maximum allowed current during normal operation (EN60601-1), thus limiting the efficiency of the circuit compared to the typically used 50 µA limit.

Considering the prior art, there also remains an unresolved technical problem relating to the changeover from 5- to 12-lead measuring mode in case of the combined collecting connector. When the ECG electrodes are initially attached to the patient and the analog switches 18-22 are open, the ECG device is capable of deducing the number of electrodes used by analyzing the signal characteristics from the different signal lines. Once the analog switches are closed, it is not possible to detect addition of precordial electrodes based on signal characteristics, there thus being no way for the amplifier to detect the addition of the precordial electrodes and this way to automatically change over from 5 to 12-lead measuring mode.

To mitigate the above-mentioned shortcoming, patent application WO 01/06923 discloses a method of detecting the addition of precordial electrodes based on a special arrangement related to the shield of the N electrode lead wire, which corresponds to the $V_6$ signal lead wire. This arrangement is not optimal because in this case the moment of change from 5 to 12-lead measuring mode in the monitor depends on the order in which the precordial electrodes are connected to the patient.

One possible solution would be to use the activation of the RLD circuit current limiting feature as an indicator of addition of a precordial electrode. This solution is not desirable, since it would be based on the relatively low 10 µA current limit setting. Furthermore, the connection of a precordial electrode would make the RLD circuit temporarily inoperable.

PURPOSE OF THE INVENTION

The purpose of the invention is to overcome the above described drawbacks related to the alternate use of connector elements in an ECG connector either for ECG recording or lead wire shield grounding.

SUMMARY OF THE INVENTION

In accordance with the invention, analog switches are used to couple the shields of the electrode lead wires not directly to the amplifier ground, but to an electronics circuit (shield grounding circuit) which has output properties that provide sufficient grounding of the lead wire shields, limit the current during normal operation, and enable detection of the addition of precordial electrodes.

In the preferred embodiment of the invention the shield grounding circuit is a constant voltage source with a current limiting feature. In case one or multiple precordial electrodes are added to the monitoring setup, this kind of circuit draws a constant DC current from the RLD circuit, but does not make it inoperable. The addition of the precordial electrode(s) can be detected either based on the current limiting feature or by analysis of recorded ECG from the precordial electrode(s).

Furthermore, in one embodiment of the invention the addition of the precordial electrode(s) can be detected using a voltage comparison and, thus comparing the voltage over current limiting resistor or component to the predefined reference voltage. As soon as the voltage over the resistor exceeds the certain limit the addition can be detected.

In one embodiment of the invention the grounding circuit consists of one or more passive components, like simple resistors, or resistors and capacitors to further tailor the frequency response of the circuit. The circuit may also include one or more non-linear components, such as spark gaps or diodes. The DC and AC impedance of the system has to be large enough to keep the current within the safety limits under all conditions.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Figure 1:
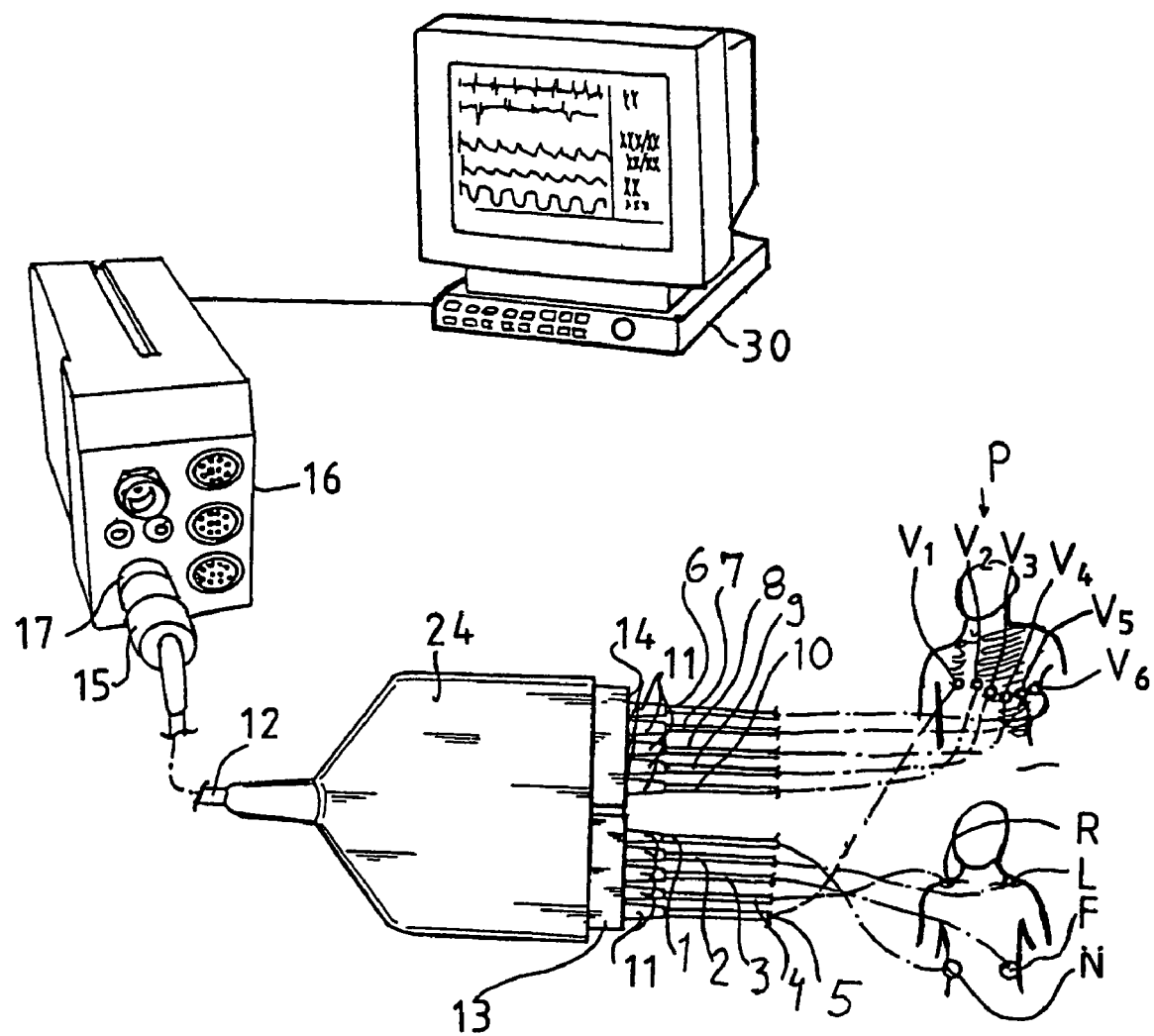
FIG. 1 is a diagrammatic representation of prior-art system.
Figure 2:
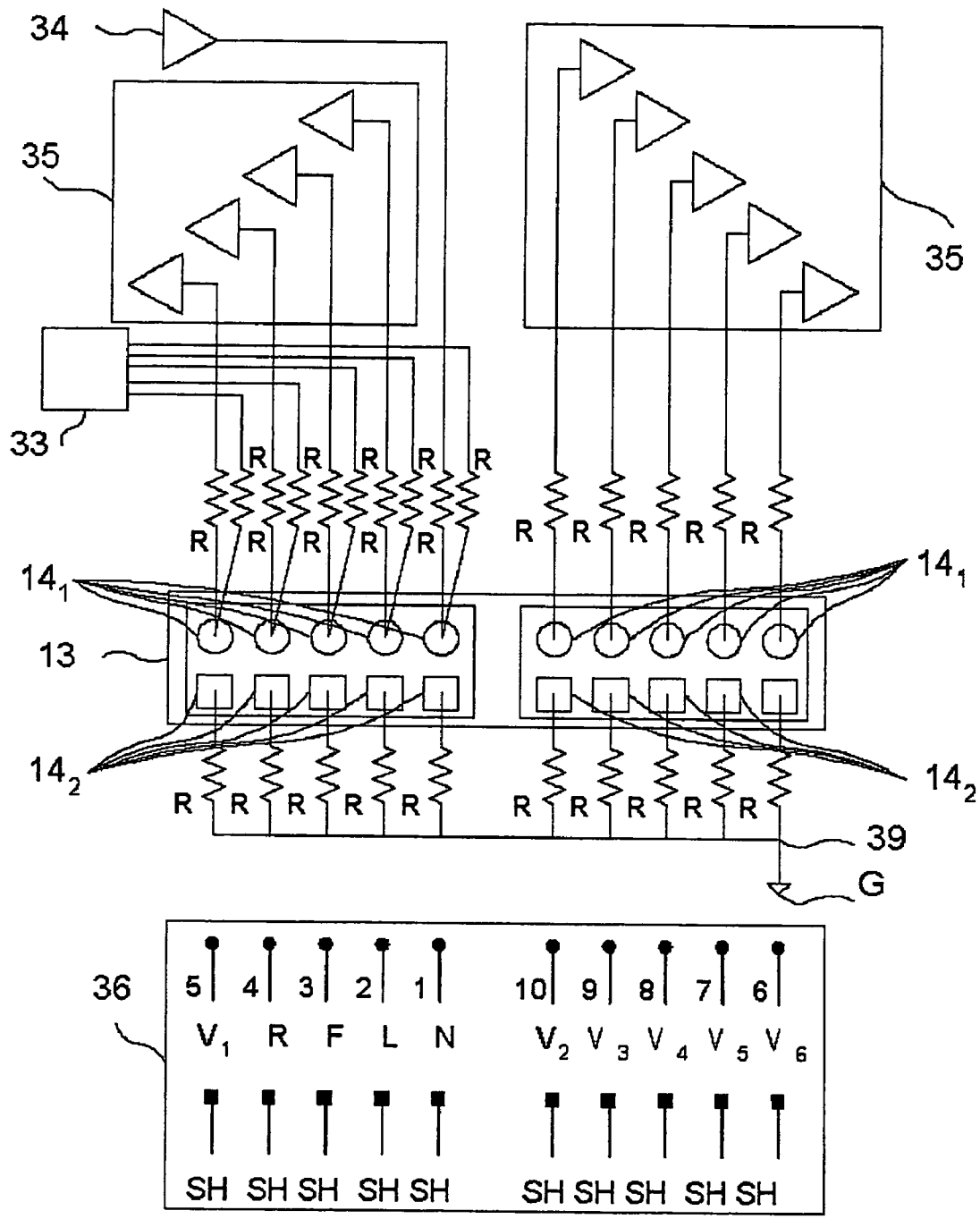
FIG. 2 is an example of the circuitry of the system presented in FIG. 1.
Figure 3:
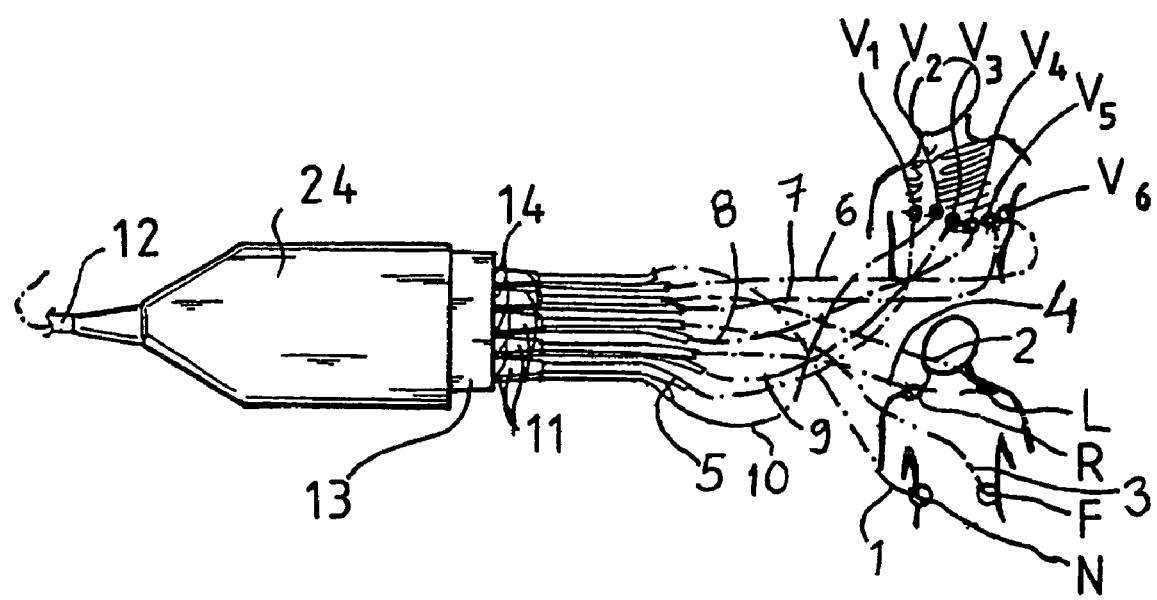
FIG. 3 is a diagrammatic representation of another prior-art system, which the present invention is related to, FIG. 4 is one embodiment of the circuitry of the system presented in FIG. 3 enhanced with the present invention.
Figure 4:
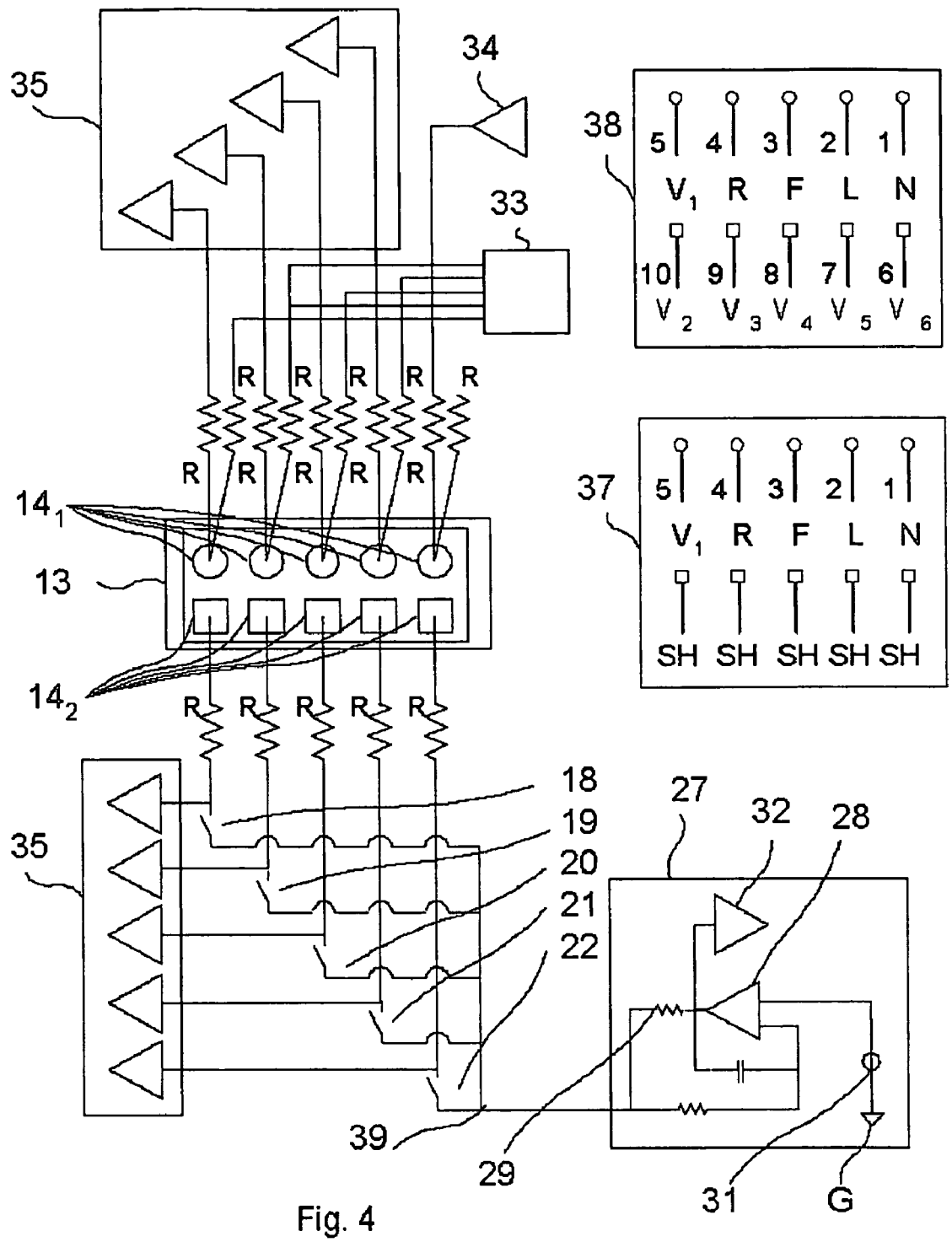

Reference will now be made in detail to the embodiments of the present invention. FIG. 4 represents a complete system in which a shield grounding circuit 27 according to the invention is applied to prior art system.

As shown in FIG. 4, the collecting connector 13 in the prior art embodiment contains a number of connector elements 14; $14_1$, $14_2$ corresponding to the number of measuring electrodes defined in the 12-lead ECG standard, i.e. a total of 10 connector elements. As can be seen, the connection elements for the lead wires 1-4 connected to the limb electrodes R, F, L, N and for one lead wire 5 of the precordial electrode $V_1$ are arranged in the upper first row $14_1$ in the collecting connector 13. The connection elements for the rest of the lead wires 6-10 connected to the rest of the precordial electrodes $V_2$, $V_3$, $V_4$, $V_5$, $V_6$ are arranged in the lower second row $14_2$ in the collecting connector 13 the second row $14_2$ being in paired alignment with said first row.

The electronics of the amplifier unit in FIG. 4 is provided with analog switches 18-22 controllable by the microprocessor of the ECG apparatus (not shown). If the analog switches 18-22 are in "open" connection positions, the measurement signals are passed from all the measuring electrodes R, F, L, N; $V_1$, $V_2$, $V_3$, $V_4$, $V_5$, $V_6$ in the 12-lead set 38 to the preamplifiers 35 and further to the signal processing stage in the ECG apparatus (not shown). In the "closed" connection positions the analog switches 18-22 establish a connection between the second group of connector elements 142 in the lower second row of the collecting connector 13 and the shield grounding circuit 27. When the analog switches 18-22 are in the "closed" connection position, the second group of connector elements $14_2$ can be used for providing shielding ground connections for possible electrostatic shield over the 5-lead system 37 lead wires 1-5 connected to the upper first row $14_1$.

With this arrangement, both 5 and 12-lead ECG measuring modes can be used with the same compact collecting connector which resembles a conventional existing collecting connector designed for a 5-lead system, which means in practice that the shielding ground connections 142 of the 5-lead system 37 are utilized by the precordial electrodes $V_2$, $V_3$, $V_4$, Vs, $V_6$ of the 12-lead system 38 as signal lines. In the 12-lead measuring mode, the signal lead wires are used without shielding ground connections, whereas in the 5-lead measuring mode the existing signal lead wires are used with shielding ground connections as usual.

Block 27 in FIG. 4 illustrates the preferred embodiment of the invention, in which shield ground connection 39 is directed to the shield grounding circuit block 27.

The electronics in the shield grounding circuit 27 is built around an operation amplifier 28, the circuit operating as a voltage buffer. The output impedance of this buffer shall be relatively low, e.g. less than 10 kohm, preferably over the whole frequency range of the ECG signal, e.g. 150 Hz, or at least over the line voltage frequency, i.e. 50 Hz, as long as the current at the output of the shield grounding circuit is below a predefined limit, e.g. 10 μA. If current in the output exceeds this limit, the output impedance of the circuit goes very high, thus limiting the current to the predefined value.

In block 27 resistor 29 acts as a current limiting component. During normal operation electric fields coupling to the lead wire shields generate currents that are significantly smaller than the above mentioned current limit, the amplifier thus remaining in low output impedance mode.

The reference voltage to this buffer is DC voltage 31. This DC voltage is selected to be slightly different from the target value of the RLD-circuit. It may even be nominally the same, but in practice also this results to the desired behavior, because of non-idealities like offset voltages in the amplifier components. Initially, the potential of the patient in respect to the amplifier ground is set to target value of the RLD circuit. When at least one precordial electrode is added, a DC current flows from the RLD to the shield grounding circuit. This current is limited to the value determined by the shield grounding circuit 27. If this current limit (typically 10 μA) is lower than the current limit in the RLD circuit (typically 50 μA), the ECG measurement is not disturbed by these events.

The addition of a precordial electrode can be easily detected by observing the state of current limit of the shield grounding circuit, which is activated. Considering the circuit in block 27, this is performed by monitoring the output voltage of amplifier 28, which is driven to either upper or lower rail. The monitoring can be done using the voltage comparator 32 that will give an output signal indicative of the exceeding of the reference voltage. This signal is led to the ECG monitoring device (not shown). This detection mechanism is sensitive to a change in any of the precordial lead wires, thus enabling the monitor to change mode immediately independent of the order in which the precordial electrodes are attached to the patient.

The invention is not restricted to the above represented example but the other applications of the invention according to the inventive step of the patent claims are possible.

The invention claimed is:

1. Grounding circuitry suitable for use with ECG signal acquisition conductors providing ECG signals acquired from a patient to an electrocardiograph, said conductors including at least a first set of ECG signal conductors for connection to the patient and suitable for carrying out ECG signal acquisition from the patient of a given number of leads, said grounding circuitry also being suitable for use with a second set of ECG signal conductors for connection to the patient, said second set of conductors being suitable for carrying out, with said first set of conductors, ECG signal acquisition from the patient of a greater number of leads than said given number of leads, said circuitry comprising:

switch means, said switch means being suitable for connection to the ECG signal conductors of the second set of conductors, when present, and having a first condition that connects the conductors of the second set to an output for providing ECG signal acquisition of said greater number of leads to the electrocardiograph, said switch means having a second condition; and a grounding circuit having a first terminal connectable to ground and a second terminal, said grounding circuit comprising means for creating low impedance path between said first and second terminals when in a first state and for creating a high impedance path between said first and second terminals when in a second state;

said switch means when in the second condition, disconnecting conductors of the second set from said output and connecting the conductors of the second set to said second terminal of said grounding circuit, said grounding circuit means being responsive to the presence of current in the second set of conductors when said second set of conductors is connected to said second terminal for assuming said first, low impedance path state when the current at said second terminal is below a predefined limit for holding the conductors of the second set at the potential of the ground, said grounding circuit means assuming said second, high impedance path state when the current at said second terminal is in excess of the predefined limit for limiting the amount of current to which the patient is exposed if a conductor of said second set is connected to the patient.

2. The grounding circuitry of claim 1 wherein said grounding circuit means comprises an operational amplifier interposed between said first and second terminals.

3. The grounding circuitry of claim 1 wherein said grounding circuit means includes means for sensing an operating condition of the grounding circuit means when said grounding circuit mean is in said second state for determining that an electrode of the second set is connected to the patient.

4. The grounding circuitry of claim 3 wherein said sensing means comprises voltage comparison means.

5. The grounding circuitry of claim 3 wherein said sensing means causes said switching means to switch from said second state to said first state when it is determined that an electrode of the second set is connected to the patient.

6. The grounding circuitry of claim 1 wherein said grounding circuitry is suitable for use with a first set of ECG signal conductors having shields and wherein said switch means the shields of the first set of ECG signal conductors to said second terminal of said grounding circuit when said switch means is in said second condition for holding the shields at the potential of the ground.

7. The grounding circuitry of claim 1 wherein said switch means is connected to a collection connector suitable for connection to the conductors of said first and second sets.

8. The grounding circuitry of claim 6 wherein said switch means is connected to a collection connector having connector suitable for connection to the conductors of said first set and connectors suitable for connection to either the shields of the conductors of said first set or the conductors of said second set.

9. The grounding circuitry of claim 1 further defined as suitable for use with a first set of EGG signal conductors suitable for carrying out 5-lead ECG signal acquisition and a second set of ECG signal conductors suitable for carrying out 12-lead ECG signal acquisition.

* * * * *